United States Patent [19]

Gabas

[11] Patent Number: 5,004,138
[45] Date of Patent: Apr. 2, 1991

[54] AUTOMOBILE SUN VISOR WITH BUILT-IN AIR FRESHENER BOX

[75] Inventor: Carlos Gabas, Barcelona, Spain

[73] Assignee: Industrias Techno-Matic S.A., Barcelona, Spain

[21] Appl. No.: 431,923

[22] Filed: Nov. 6, 1989

[30] Foreign Application Priority Data

Nov. 7, 1988 [ES] Spain .............................. 8803274[U]

[51] Int. Cl.$^5$ .............................................. A61L 9/12
[52] U.S. Cl. ............................ 224/312; 224/42.042; 239/55; 239/57; 239/59; 296/97.005; 296/37.008
[58] Field of Search ............. 224/312, 311, 328, 42.42; 239/44, 47, 51.5, 55, 56, 57, 58; 296/37.7, 37.8, 97.5

[56] References Cited

U.S. PATENT DOCUMENTS

| | | | |
|---|---|---|---|
| 4,258,004 | 3/1981 | Valenzona et al. | 239/57 X |
| 4,352,457 | 10/1982 | Weick | 239/47 X |
| 4,521,051 | 6/1985 | Cody et al. | 224/312 X |
| 4,523,870 | 6/1985 | Spector | 239/57 X |
| 4,648,011 | 3/1987 | Boote et al. | 296/97.5 X |
| 4,781,409 | 11/1988 | Harbison | 224/312 X |
| 4,814,212 | 3/1989 | Spector | 239/57 X |
| 4,815,659 | 3/1989 | Turko et al. | 239/58 X |

Primary Examiner—Ernest G. Cusick
Attorney, Agent, or Firm—Michael J. Striker

[57] ABSTRACT

The automobile sun visor with built-in air freshener box has a sun visor body with a hollow container mounted in a recess therein so as to be incorporated in the sun visor body with its upper edges near the surface of the visor body. The hollow container has opposing lateral guideways close to opposing upper edges of the container and is provided with a cover slidably mounted in the lateral guideways. The guideways have extensions extending beyond the container sufficiently to allow for a major portion of the cover to be received in the extensions when the container is opened. The hollow container may also be provided with a number of outwardly directed projecting members which hold an air freshener element and the cover may be provided with holes for emission of a fragrance. Structural reinforcement structure is provided for maintaining an appropriate solidity and rigidity of the extensions of the guideways. The structure reinforcement structure may be rails associated with the guideways and a cross wall connecting the rails.

5 Claims, 2 Drawing Sheets

AUTOMOBILE SUN VISOR WITH BUILT-IN AIR FRESHENER BOX

BACKGROUND OF THE INVENTION

The object of the invention is a box for housing an air freshener element with a solid support, forming part of the structure of the sun visors with which automobiles are usually equipped. The broad possibilities of incorporating more or less complex ancillary, complementary items that aid in driving or make the stay inside the vehicle more comfortable and pleasant, are already known. The present invention relates precisely to a novel embodiment which is original in design, conception and functionality based on a box which may be incorporated in sun visor structures, with a special novel functionality and utility.

The use in automobiles of aromatic chemicals directed to neutralizing both the characteristic smells of new vehicles and those generated in normal use is well known. The means used hithertofore for this purpose consisted basically of solid or liquid aromatic substances in many forms and on many carriers, which are placed inside the vehicle, either by attachment to the bodywork by adhesives or simply hanging them in more or less accessible or totally inadequate places as far as the occupants' security is concerned. Nevertheless, the inventor is not aware of any prior reference to devices of like or similar features to those of the present invention.

SUMMARY OF THE INVENTION

It is an object of my invention to provide an automobile sun visor with a built-in box for air freshener products.

The air freshener box according to the invention provides the following main advantages:

(A) it may be adapted to the sun visor structure, independently of the side of the vehicle in question;

(B) it has a design allowing any appropriate air freshener element to be housed, fixed, concealed and replaced with extreme ease;

(C) the air freshener element is concealed by a cover designed for the purpose which slides on guideways provided in the main body of the box;

(D) the cover mentioned in (C) above is provided with orifices that allow issue of the air freshener product aroma; this effect is enhanced by the very fact that the sun visor is regularly located in the area where the air flow from the front inner ventilation means of automobiles converges, so that the air flow entrains said aroma and thus provides for its extensive speedy diffusion throughout the whole of the vehicle.

It is essentially characteristic of the air freshener box according to the invention that it is essentially formed by a main hollow container or body having an essentially parallelepiped or other appropriate shape incorporated in the structure of an automobile sun visor. This container is generally aligned with one of the main axes of the sun visor and is provided with a sliding cover mounted on respective lateral guideways located close to the upper edge of the container. These guideways extend beyond the container's edge sufficiently to allow the location of a major portion of the cover's length when moved in an opening operation.

In the automobile sun visor with built-in air freshener box according to the present invention the air freshener box is mounted in a box recess provided in sun visor body. The air freshener box is aligned with a main or major axis of the air freshener box.

The sun visor structure according to the invention also includes structural reinforcement means which ensure and maintain an appropriate solidity and rigidity of the portions of the lateral guideways that extend beyond the perimeter of the main body and on which the air freshener box cover slides.

It is understood that this structure reinforcement means may be of different types, such as rails for the extensions of the guide ways, a cross wall connecting the rails, cross-members, gussets, plates and others of different shapes which will be selected depending on the particular form to be manufactured.

It is a further feature of the air freshener box according to the invention that it is provided with a plurality of outwardly projecting members which may be located in different positions to hold or fix the air freshener element.

The container is, of course, designed in principle to universally accept a variety of differently shaped air freshener elements. With this end in mind, attachment means are contemplated for the air freshener element, without eliminating the possibility of providing, in certain cases, attachment or holding means specifically devised for particular types of air freshener elements.

The air freshener box according to the invention is also characterised in that the cover thereof is provided with aeration orifices that facilitate the diffusion of the air freshener aroma through the interior of the vehicle. It is also provided with a means to allow the user to move the cover. The means is generally a projecting piece or handle which may be easily manipulated with the fingers.

BRIEF DESCRIPTION OF THE DRAWINGS

The objects, features and advantages of the present invention will now be illustrated in more detail by the following detailed description, reference being made to the accompanying drawing in which.

DETAILED DESCRIPTION OF THE INVENTION

Figure 1:
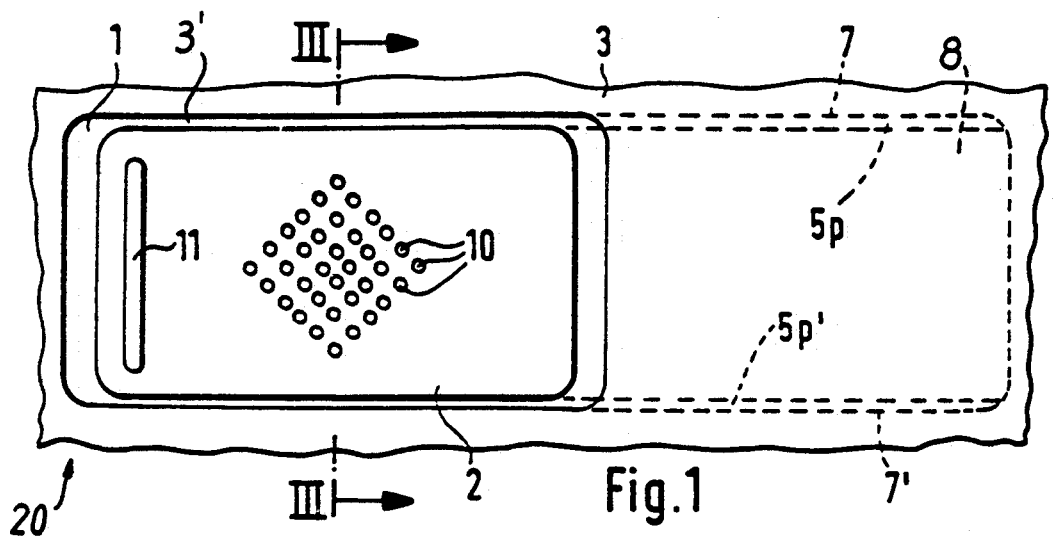
FIG. 1 is a cutaway plan view of an automobile sun visor with built-in air freshener box according to may invention with the cover closed.

The automobile sun visor with built-in air freshener box of the invention as embodied in the accompanying drawing, is formed essentially by a main hollow container 1 and a cover 2 thereof, both of which are made from material appropriate for its contemplated use and purpose, and can be adapted to the sun visor body 3.

The hollow container 1, with its cover 2, is incorporated as original equipment, i.e. by the manufacturer, in the sun visor body 3 in a suitable box recess 3' for which purpose it is provided with the means and/or configurations deemed to be most desirable in each case.

The container 1 has, in the present embodiment, an essentially parallelepiped shape and is aligned with a main axis 3" of the sun visor body. The container 1 will appropriately house the air freshener element 4. Likewise, both the shape and the surface 3" of the sun visor body bounding the access to the interior of the container 1 are appropriate for allowing the operations that the user has to carry out with the air freshener element 4 in regular conditions of use.

The cover 2 is moveable. So that it may slide easily when being moved during the opening and closing operations of the container 1, opposing lateral guideways 5 and 5' have been provided close to opposing upper edges 6 of the container. When the container is provided with straight, parallel edges, as is the case of the embodiment illustrated in, the drawings, the guideways 5—5' may be placed on the same inner wall of the container itself. When the container is oval or circular, corresponding rail-like projections to carry the guideways 5—5' will be provided. Furthermore, in all cases (parallelepiped, oval or circular container 1), the guideways 5 and 5', are continued in corresponding extensions 5p and respectively 5p' beyond the container 1 to be able to admit almost the whole length of the cover 2 when the container 1 is being opened. These extensions 5p—5p' of the guideways 5—5' generally require reinforcement means to ensure the positional stability and strength thereof. In the embodiment shown, the rails 7—7' and the cross wall 8 have been used as reinforcements. It may be appreciated that said rails 7—7' extend to a length such that the cover 2 moves beyond the container 1 in the opening movement, defining a sliding plane of the cover 2 essentially parallel to the base plane of the ensemble of the invention. Both longitudinal and transverse ribs may be provided with appropriate dimensions to ensure that the ensemble is suitably rigid.

Figure 2:
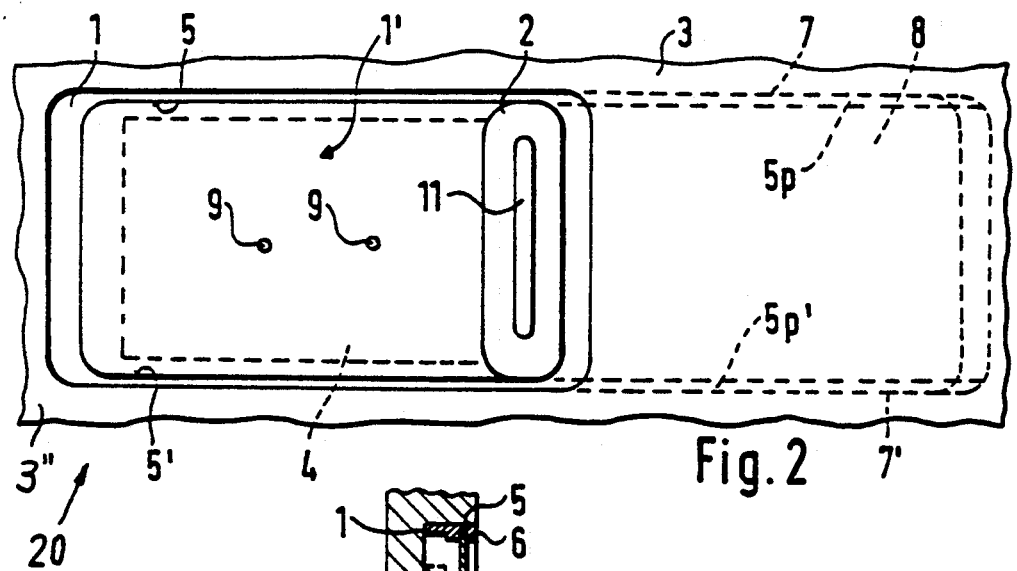
FIG. 2 is a cutaway plan view of an automobile sun visor with built-in air freshener box with the cover open.
Figure 3:
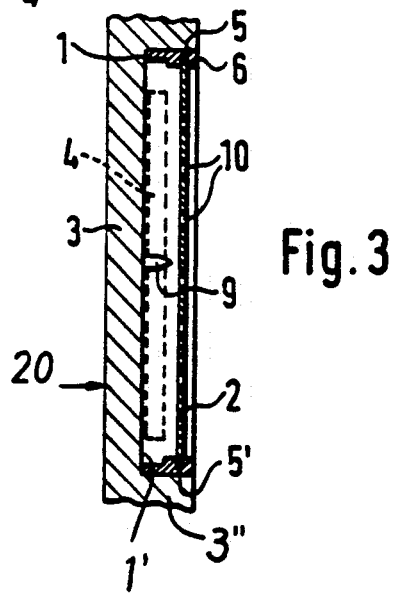
FIG. 3 is a cross sectional view of the automobile sun visor taken along the section line III—III of FIG. 1.
Figure 4:
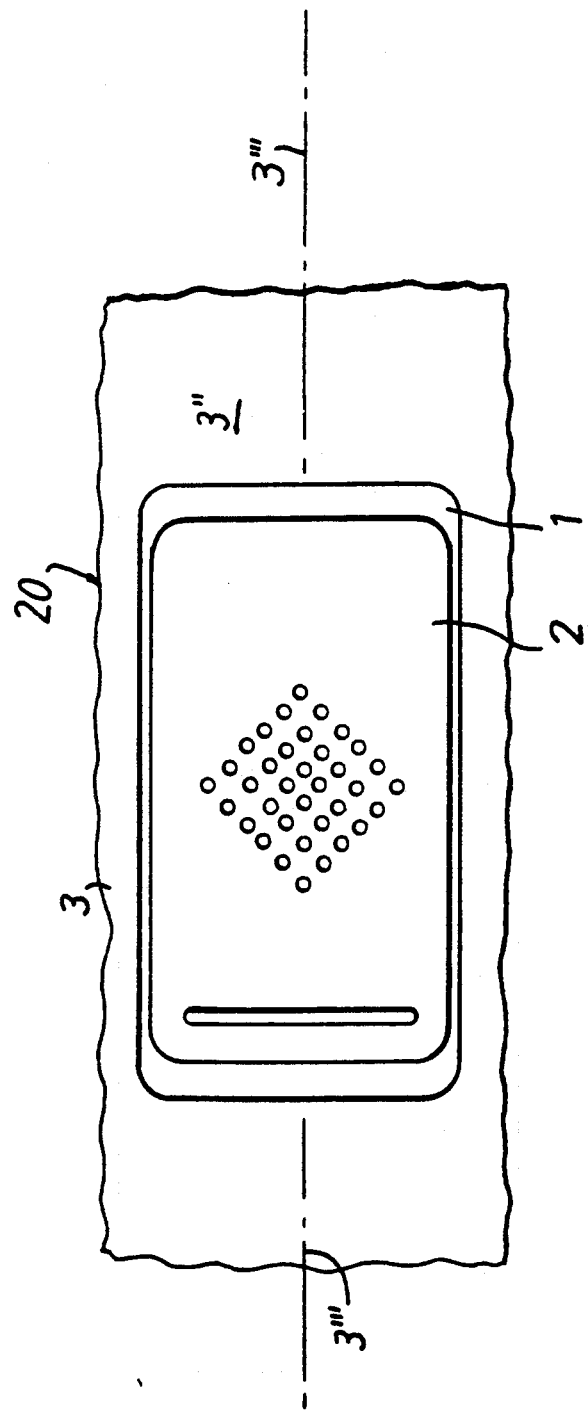
FIG. 4 is a plan view of the automobile sun visor with built-in air freshener box aligned on a main axis of the sun visor.

The container 1 is also provided with two projecting members 9 that attach the air freshener member 4, thereby using the mechanical parts or elements of these air freshener elements. Such projecting members, as may be seen in FIG. 2, are preferably located in the center portion of the bottom 1' of the container 1.

The cover 2, as described above, is fitted by way of the guideways 5 and 5' to the main body 1 and is essentially rectangular in shape. To facilitate the sliding movement thereof by the user, it includes th handle 11.e The cover 2 is also provided with ventilation holes 10 which both in number and distribution facilitate the diffusion of the aromatic product throughout the interior of the vehicle.

It will be understood that each of the elements described above, or two or more together, may also find a useful application in other types of structures differing from the type described above.

While the invention has been illustrated and described as embodied in an automobile sun visor with built-in air freshener box, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of the prior art, fairly constitute essential characteristics of the generic or specific aspects of this invention.

What is claimed as new and desired to be protected by Letters Patent is set forth in the appended claims.

I claim:

1. Automobile sun visor with built-in air freshener box comprising a sun visor body provided with a box recess and a body surface and having a main axis and a main hollow container having a plurality of upper edges, said hollow container being mounted in said box recess so as to be incorporated in said sun visor body with said upper edges in the vicinity of said body surface, said container being generally aligned with said main axis of said sun visor body and said hollow container having opposing lateral guideways adjacent opposing ones of said upper edges and being provided with a sliding cover mounted in said lateral guideways located close to said upper edges, said guideways having extensions extending beyond said container sufficiently to allow for a major portion of said cover to be received in said extensions, when said cover is moved in an opening direction, and said hollow container also being provided with means for holding an air freshener element in said hollow container.

2. Automobile sun visor with built-in air freshener box according to claim 1, further comprising structural reinforcement means associated with said extensions which ensure and maintain an appropriate solidity and rigidity of the extensions of the guideways extending beyond a perimeter of the hollow container.

3. Automobile sun visor with built-in air freshener box according to claim 1, further comprising said air freshener element and wherein said means for holding said air freshener element comprises a plurality of outwardly projecting members by which said air freshener element is retainable.

4. Air freshener box according to claim 1, wherein said cover is provided with a plurality of ventilation orifices that facilitate emission of a freshener aroma, and further comprising a handle for moving said cover.

5. Automobile sun visor with built-in air freshener box, comprising a sun visor body provided with a box recess and a body surface and having a main axis, and a main hollow container having a plurality of upper edges, said hollow container being mounted in said box recess so as to be incorporated in said sun visor body with said upper edges in the vicinity of said body surface, said container being generally aligned with said main axis of said sun visor body, and said hollow container having opposing lateral guideways adjacent opposing ones of said upper edges and being provided with a sliding cover mounted in said lateral guide ways located close to said upper edges, said guideways having extensions extending beyond said container sufficiently to allow for a major portion of said cover to be received in said extensions, when said container is opened, and said hollow container also being provided with a plurality of outwardly projecting members by which an air freshener element is retainable; and structural reinforcement means connected with said extensions for maintaining an appropriate solidity and rigidty of the extensions of the guideways, said structural reinforcement means being rails extending beyond a perimeter of the hollow container and a cross wall connecting the rails.

* * * * *